United States Patent [19]

Williams et al.

[11] Patent Number: 4,553,957
[45] Date of Patent: Nov. 19, 1985

[54] IRRIGATION/ASPIRATION HANDPIECE

[75] Inventors: Rodger W. Williams; Charles W. Atwood, both of Nashville, Tenn.

[73] Assignee: Alcon Laboratories, Inc., Fort Worth, Tex.

[21] Appl. No.: 491,222

[22] Filed: May 3, 1983

[51] Int. Cl.$^4$ .............................................. A61M 3/00
[52] U.S. Cl. ..................................... 604/43; 604/902
[58] Field of Search ....................... 604/22, 27, 35, 39, 604/43–45, 93, 163, 171–173, 183, 257, 290, 902; 433/81, 82

[56] References Cited

U.S. PATENT DOCUMENTS

| | | | |
|---|---|---|---|
| 3,994,297 | 11/1976 | Kopf | 604/43 |
| 4,069,814 | 1/1978 | Clemens | 604/27 |
| 4,294,251 | 10/1981 | Greenwald et al. | 604/43 |
| 4,316,465 | 2/1982 | Dotson, Jr. | 604/22 |

Primary Examiner—C. Fred Rosenbaum
Assistant Examiner—J. L. Kruter
Attorney, Agent, or Firm—Holman & Stern

[57] ABSTRACT

A hand-held cannula assembly for irrigating and aspirating ophthalmic surgical sites includes an irrigation cannula circumscribed about an aspiration cannula and extending out through the forward end of the assembly from a reservoir for the irrigation fluid in the handle. Pressurized irrigation fluid is supplied to the reservoir through the rearward end of the handle and flows through openings in the irrigation cannula periphery into an annular flow passage between the two cannulas. An opening in the irrigation cannula issues the irrigation fluid at the surgical site. Aspiration fluid is drawn into the aspiration cannula which extends through the handle interior to an outflow opening at the rearward handle end.

20 Claims, 5 Drawing Figures

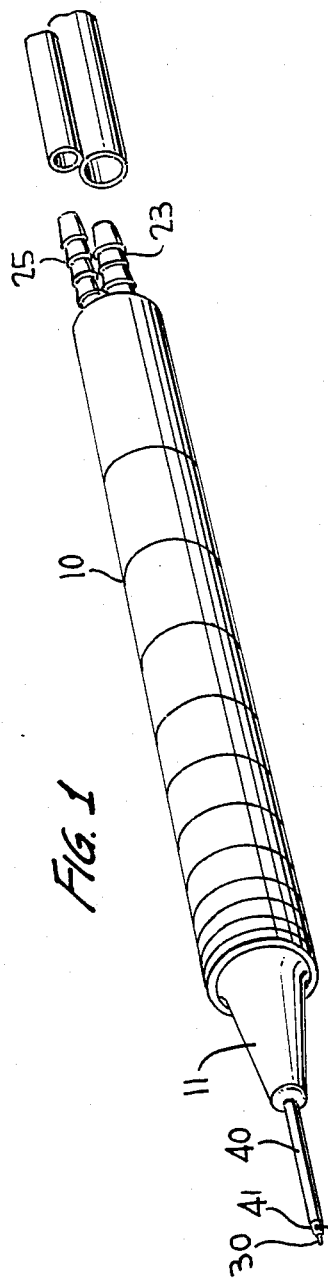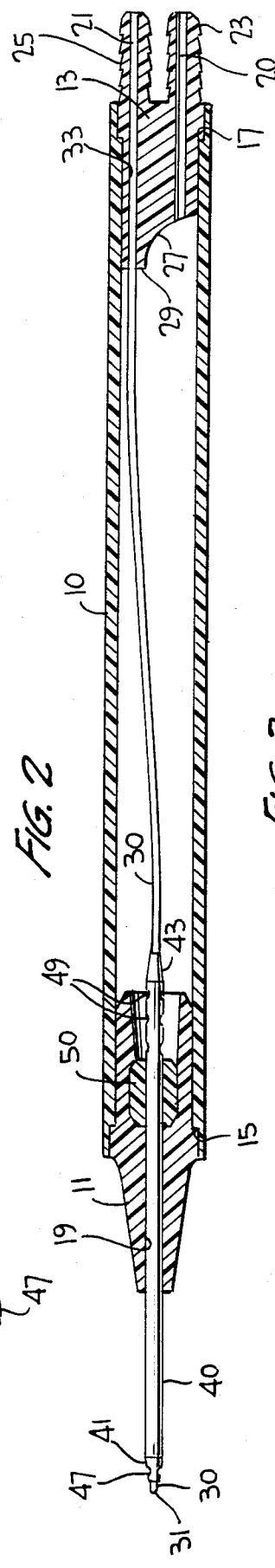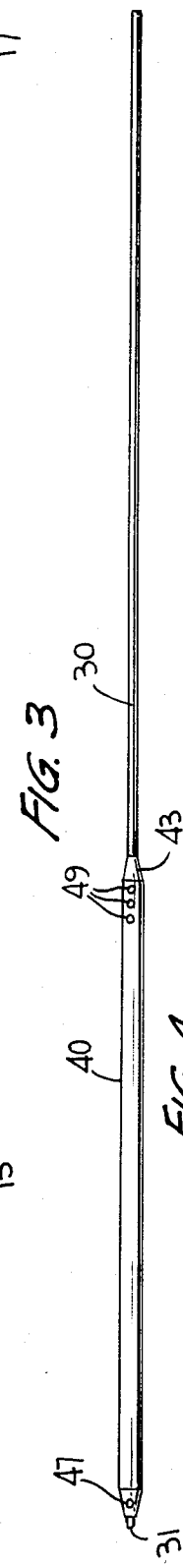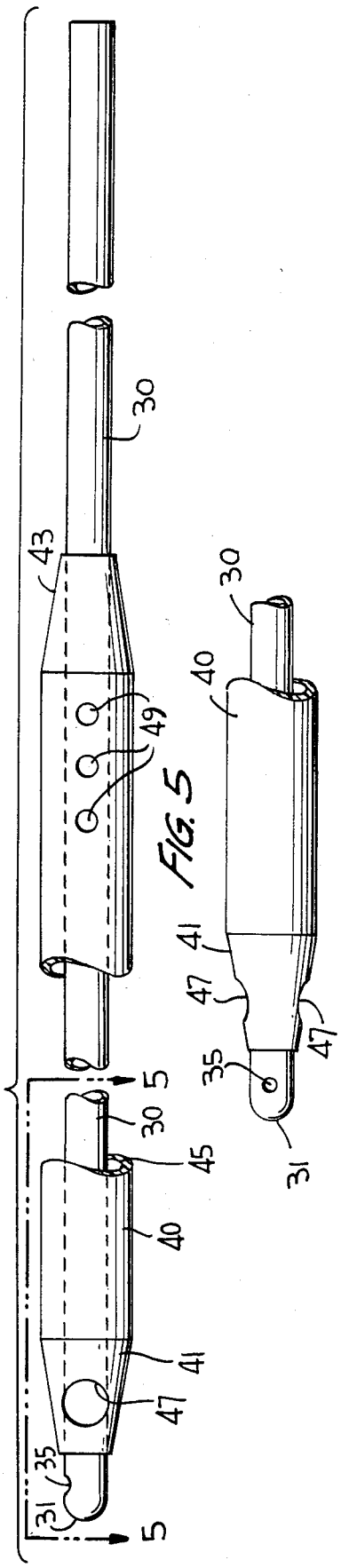

IRRIGATION/ASPIRATION HANDPIECE

BACKGROUND OF THE INVENTION

1. Technical Field

The present invention relates to cannulas for simultaneously transporting fluids in opposite directions to and from a surgical site. More particularly, the present invention relates to a cannula assembly for simultaneously aspirating and irrigating an ophthalmic surgical site.

2. The Prior Art

In certain ophthalmic surgical procedures, such as extracapsular cataract extraction, it is required that the surgical site be simultaneously irrigated and aspirated. Hand-held cannula assemblies for performing these functions have been commercially available for some time. One such assembly, which is widely used, includes a generally cylindrical handle having concentric steel tubes projecting from its forward end. The inner tube serves as an aspiration cannula and extends into the handle interior where it is soldered to a narrow connection tube which, in turn, connects to a plastic tube. The latter extends out to the rearward end of the handle to a suction device. The outer steel tube serves as the irrigation cannula and has a tapered forward end which contacts and is soldered to a section of the aspiration cannula periphery. An egress opening in a forward tapered section delivers pressurized irrigation fluid to the surgical site from the annular flow space between the two cannulas. Irrigation fluid is delivered axially into this annular flow space from another narrow connection tube which is soldered to the two cannulas and to the aspiration connection tube. The irrigation connection tube receives pressurized irrigation fluid from a plastic tube which extends parallel to the plastic aspiration tube and out through the rearward end of the handle to a source of pressurized fluid. The two narrow connection tubes are difficult to assemble to the rearward end of the cannulas because of the small sizes of the cannulas and the connection tubes. In addition, the soldered joint, wherein both connection tubes communicate axially with respective cannulas, requires one or both of the connection tubes to be bent off-axis in order that each can be properly oriented with respect to its cannulas and soldered in place. This cannula bending and connection tube placement in the cylindrical handle radially enlarges the interior space required for the soldered joint, thereby requiring the handle diameter to be larger than would otherwise be necessary so that the joint may be accommodated. As a general rule, ophthalmic surgeons prefer a smaller diameter handle, both for ease in manipulating the device and for providing maximum visible access to the surgical site.

OBJECTS AND SUMMARY OF THE INVENTION

It is therefore an object of the present invention to provide an improved irrigation/aspiration unit for ophthalmic surgical procedures which can be simply and quickly fabricated.

It is another object of the present invention to provide a hand-held irrigator/aspirator for use in ophthalmic surgery wherein the handle can be fabricated with a reduced diameter as compared to prior art units of this general type.

Still another object of the present invention is to provide an irrigator/aspirator which is inexpensive and simple to fabricate and is easier to use than are prior art units of this general type.

In accordance with the present invention, irrigation fluid is conducted via the handle interior into peripheral inlet openings in the outer or irrigation cannula while the aspiration cannula extends entirely through the handle to a fitting at the rearward handle end. The irrigation cannula tapers at both ends to be sealed against the inner or aspiration cannula. Inflow to the annular irrigation fluid passage from the handle interior is thus radially, rather than axially, directed and the soldered connection tube joint employed in the prior art is eliminated. The resulting unit has fewer parts to assemble and the assembly is easily and quickly effected. No internal cannula bends or internal tube connection placement mandate the minimum handle diameter which can be reduced significantly with the present invention as compared to the prior art units.

BRIEF DESCRIPTION OF THE DRAWINGS

These and other objects, features and many of the attendant advantages of the invention will be better understood upon a reading of the following detailed description when considered in conjunction with the accompanying drawings wherein like parts in each of the several figures are identified by the same reference numerals and wherein:

FIG. 1 is a view in perspective of an irrigator/aspirator constructed according to the present invention;

FIG. 2 is a view in longitudinal section of the irrigator/aspirator of FIG. 1; FIG. 3 is a side view of the cannula assembly employed in the irrigator/aspirator of FIG. 1;

FIG. 4 is an enlarged, partial broken side view of the cannula assembly of FIG. 3; and FIG. 5 is a top view taken along lines 5—5 of FIG. 4.

DESCRIPTION OF THE PREFERRED EMBODIMENT

Referring to the drawings in greater detail, a preferred embodiment of the irrigator/aspirator of the present invention includes a handle member in the form of a cylindrical elongated tube 10, a forward end or nose plug 11 and a rearward end or tail plug 13. Tube 10 is a hollow cylinder having an annular shoulder 15 defined in its inner wall facing and a short axial distance from the forward end of the cylinder. A similar rearward-facing annular shoulder 17 is defined in the interior wall of the cylinder at a short axial distance from the rearward end of the unit. The forward end plug 11 has an outer peripheral shoulder defined therein which mates with shoulder 15 when plug 11 is forced into the forward end of cylinder 10 in a friction fit engagement. The forward end plug 11 has a tapered forward end which projects forwardly of the cylinder and a generally cup-shaped rearward end which is disposed inside the cylinder with the open end of the cup facing rearwardly. A bore 19 extends longitudinally through forward end plug 11 and is substantially concentrically disposed about the longitudinal axis of cylinder 10. The tail plug 13 has a forward facing annular shoulder which mates with shoulder 17 of cylinder 10 when the tail plug 13 is forced into the rearward end of cylinder 10 in a friction fit engagement. An inlet bore 20 is defined longitudinally through the tail plug 13 in generally parallel relation to the longitudinal axis of cylinder 10. An outlet bore 21 is defined through tail plug 13 parallel to bore 20 and to the longitudinal axis of cylinder 10.

The rearward end of tail plug 13 terminates in two barbed fittings 23 and 25 through which the bores 20 and 21, respectively, extend. The forward end of tail plug 13 includes a generally concave surface 27 at which bore 20 terminates and a flat section 29 at which bore 21 terminates. The barbed fittings 23, 25 are adapted to be connected to respective plastic tubes for the purpose described hereinbelow.

An aspiration cannula 30 takes the form of an elongated stainless steel tube having a forward end 31 and a rearward end 33. The rearward end 33 of cannula 30 is engaged in a friction fit in bore 21 of the tail plug 13. Aspiration cannula extends from the tail plug through the interior portion of hollow tube 10 to the forward end plug 11 where it passes through the bore 19 to a position beyond the forward end of plug 11. The rearward end 33 of cannula 30 is open to provide axial flow communication between it and the bore 21. The forward end 31 of cannula 30 is closed; however, an aspiration port 35 is defined in the periphery of cannula 30, proximate forward end 31, and has an axis which is oriented generally perpendicular to the longitudinal axis of cannula 30.

An irrigation cannula 40, which is much shorter in axial length than cannula 30, is disposed concentrically about cannula 30 at the forward end of handle member tube 10. Irrigation cannula 40 is a stainless steel tube of larger diameter than aspiration cannula 30 and has tapered forward and rearward ends 41 and 43, respectively. The tapered ends taper sufficiently so as to contact the periphery of aspiration cannula 30 at which points the two cannulas are soldered together. Thus, the two cannulas are spaced from one another throughout most of their common lengths and are joined only at the ends of the irrigation cannula 40. The space 45 between the two cannulas constitutes a flow path 45 of generally annular configuration. The rearward end 43 of irrigation cannula 40 is disposed inside tube 10 just rearwardly of the rearwardmost portion of forward plug 11. The forward end 41 of the irrigation cannula 40 extends beyond plug 11 to a location just rearward of the aspiration port 35 defined in the aspiration cannula 30. One or more generally circular egress holes 47 are defined in the tapered forward end portion 41 of cannula 40. A plurality of ingress holes 49 of generally circular configuration are defined in cannula 40 just forwardly of tapered rearward end 43 and at an axial location which places them generally within the cup-shaped rearward portion of plug 11.

Cannula 40 passes through bore 19 of plug 11 and is fixed in place with respect to that plug by means of a locking sleeve 50 disposed in the cup-shaped portion of the plug. Locking sleeve 50 is a generally cylindrical member with a longitudinally-extending bore in which cannula 40 is engaged in a friction fit; alternatively, adhesive material may be used to engage the sleeve 50 to cannula 40 in the necessary concentric relationship. The axial position of sleeve 50 along cannula 40 is such that it is just forward of the ingress holes 49. The periphery of sleeve 50 is of substantially the same or slightly larger diameter than the inner diameter of the cup-shaped portion of plug 11 so that the sleeve can be wedged into the closed or forward end of the cup-shaped portion to lock the cannula 40 in place with respect to plug 11 and the handle structure.

The elongated aspiration cannula 30 is caused to bend slightly in extending from rearward end 43 of irrigation cannula 40 to the bore 21 defined in tail plug 13. This slight bend is fully within the flexibility of the elongated cannula 30 and does not add any width to tube 10.; nor is there any restrictive effect on aspiration flow rate.

In operation, irrigation fluid is supplied via a suitable tube connected to barbed fitting 23 to the interior of handle tube 10 which serves as a reservoir for the supplied pressurized fluid. The pressurized fluid is passed into the annular passage 45 between the two cannulas by means of the ingress holes 49 in cannula 40. The irrigation fluid is issued at the surgical site through egress holes 47 defined in the tapered forward end 41 of the irrigation cannula 40. Aspiration fluid is drawn into the aspiration port 35 by means of a suction created through a suitable plastic tube connected to barbed fitting 25. The aspirated fluid is conducted through the aspiration cannula 30 and out through the bore 21 to the connected tube.

The apparatus as described hereinabove eliminates the need for difficult solder connections for the flow paths for the two cannulas. Elimination of these space-consuming and difficult to fabricate soldered joints and attendent tube connections is achieved by providing ingress ports 49 in the periphery of the irrigation cannula so as to deliver the irrigation fluid radially into the passage 45 rather than axially at a location adjacent the axial flow through the aspiration cannula. In order to do this, the interior of handle 10 is made to serve as a reservoir for the pressurized irrigation fluid to be delivered to the ingress ports 49.

It will be noted that a minimum number of parts are required to fabricate the preferred embodiment of the invention and that these parts are simply and inexpensively assembled to form the final units.

By way of example only, a working embodiment of the present invention has been constructed with the following dimensions. These dimensions are to be considered representative of one specific working embodiment and should not be considered as limiting the scope of the present invention. Tube 10 was made of plastic material and was four inches long and ⅜ inch in diameter. Nose plug 11 was 1⅛ inches long and made of a plastic material. Tail plug 13 was 1 inch long and made of a plastic material. The aspiration cannula 30 was made of stainless steel and was 5.05 inches long with an outer diameter of 0.032 inches and an inner diameter of 0.022 inches. The irrigation cannula 40 was a stainless steel tube having a length of 2.200 inches, an outer diameter of 0.065 inches and an inner diameter of 0.047 inches. Two holes 47 were provided in the forward end section 41 of cannula 40, each hole being spaced from the other by 180° about the longitudinal axis of the device and having a diameter of 0.035 inches. The centers of holes 47 from the forward most portion of cannula 40 was 0.037 inches. Holes 49 were made with a 0.017 inch diameter. The aspiration port 35 for aspiration cannula 30 had its center disposed 0.025 inches from the forward tip 31 of the cannula and had a diameter of 0.011 inches.

From the foregoing description it will be appreciated that the invention makes available a novel combined aspirator/irrigator for use in ophthalmic surgical procedures. The device thus provided is relatively simple in construction and convenient to use by virtue of its relatively small handle diameter.

Having described a specific embodiment of a new and improved aspirator/irrigator constructed in accordance with the present invention, it is believed that other modifications, variations and changes will be suggested to those skilled in the art in light of the above teachings. It is therefore to be understood that all such variations, modifications and changes are believed to fall within the scope of the invention as defined in the appended claims.

What is claimed is:

1. An improved apparatus for supplying fluid to and aspirating fluid from a surgical site, said apparatus comprising:
   a handle member having first and second closed opposite ends and a hollow intermediate interior means forming a resivoir
   inlet means for supplying fluid to the hollow interior portion of said handle member from said second end;
   outlet means for conducting fluid out from said second end;
   first cannula means extending from said outlet means at said second end of said handle member, through said hollow interior portion and out through said first end for aspirating fluid from said surgical site; and
   second cannula means disposed in fixed positional relation to and circumscribedly about a portion of said first cannula means and extending and terminating from within said hollow interior portion out through said first end of said handle member, said second cannula means being radially spaced from said portion of said first cannula means to define a flow passage between said first and second cannula means, said second cannula means having a first opening in fluid communication with said inlet and said flow passage positioned in fluid communication with said hollow interior means of said handle member and a second opening to said flow passage positioned outside said handle member and a second opening to said first end;
   whereby said hollow handle intermediate interior means serves as a reservoir for fluid delivered thereto from said inlet means, and whereby pressurized fluid in said hollow handle interior portion is expelled therefrom through said first opening, said flow passage and said second opening.

2. The apparatus according to claim 1 wherein said handle member comprises:
   a hollow tube having open first and second ends corresponding to said first and second ends, respectively, of said handle member;
   a tail plug member sealingly engaged in said second end of said tube and having first and second bores extending therethrough corresponding to said inlet and outlet means, respectively, wherein said first cannula means is engaged in said second bore; and
   a nose plug member sealingly engaged in said first end of said tube and having a third bore extending therethrough in which said second cannula means is engaged.

3. The apparatus according to claim 2 wherein said nose plug has a tapered forward end portion extending away from said first end of said tube, and a rearward portion which is generally cup-shaped and disposed in generally annular spaced relation about said second cannula means in said hollow handle interior portion, said apparatus further comprising a locking sleeve having a longitudinal bore extending therethrough in which a portion of said second cannula is engaged, said locking sleeve being frictionally engaged within said cup-shaped rearward portion of said nose plug.

4. The apparatus according to claim 3 wherein said second cannula means has tapered opposite end portions which contact and are secured to respective peripheral portions of said first cannula means.

5. The apparatus according to claim 4 wherein said first opening comprises a plurality of holes defined in said second cannula means rearwardly of said locking sleeve.

6. The apparatus according to claim 5 wherein said first cannula means includes an elongated tube having a longitudinal axis and a forward inlet hole formed generally perpendicular to said longitudinal axis.

7. The apparatus according to claim 6 wherein said second bore is axially misaligned with said third bore, and wherein said first cannula means bends slightly in said hollow handle interior portion in extending between said second and third bores.

8. The apparatus according to claim 7 wherein said first and second cannula means are stainless steel tubes.

9. The apparatus according to claim 7 wherein said inlet and outlet means terminate exteriorly of said handle member in respective barbed fittings adapted to be connected to plastic tubing.

10. The apparatus according to claim 1 wherein said second cannula means has tapered opposite end portions which contact and are secured to respective peripheral portions of said first cannula means.

11. The apparatus according to claim 10 wherein said first opening comprises a plurality of holes defined in said second cannula means rearwardly of said locking sleeve.

12. The apparatus according to claim 1 wherein said first cannula means includes an elongated tube having a longitudinal axis and a forward inlet hole formed generally perpendicular to said longitudinal axis.

13. The apparatus according to claim 2 wherein said second bore is axially misaligned with said third bore, and wherein said first cannula means bends slightly in said hollow handle interior portion in extending between said second and third bores.

14. Apparatus for conducting irrigating fluid to and aspirating fluid from an ophthalmic surgical site, said apparatus comprising:
   a generally cylndrical handle member having forward and rearward closed ends and an internal reservoir portion;
   an irrigation cannula. in the form of a tube secured in said forward end and extending from said reservoir to externally of said handle member through said forward end, said irrigation cannula having oppositely directed tapered ends of gradually reducing diameter;
   an aspiration cannula in the form of a tube extending concentrically within said irrigation cannula and having first and second peripheral portions secured to the tapered ends of said irrigation cannula, said irrigation cannula being annularly spaced from said aspiration cannula between said first and second peripheral portions to define an annular flow path between the cannulas, said aspiration cannula having a rearward end and a forward end extending forwardly beyond the irrigation cannula;
   an outlet passage through the closed rearward end of said handle member, wherein said rearward end of said aspiration cannula is secured in flow communication with said outlet passage; and
   inlet means for supplying irrigating fluid under pressure to said reservoir portion;

wherein said irrigation cannula has at least one inlet hole defined therein for conducting pressurized fluid from said reservoir portion into said annular flow passage, and at least one outlet hole defined therein for conducting pressurized fluid from said annular flow passage to said surgical site.

15. The apparatus according to claim 14 wherein said first and second cannulas are disposed about a common longitudinal axis and wherein said inlet and outlet holes have respective axes oriented perpendicular to said longitudinal axis.

16. The apparatus according to claim 15 further comprising a plurality of outlet holes arranged in the periphery of said irrigation cannula at angularly spaced locations about said longitudinal axis and forwardly of said forward handle member end.

17. The apparatus according to claim 16 wherein said plurality of outlet holes are disposed in one of the tapered end portions of said irrigation cannula.

18. The apparatus according to claim 15 further comprising a plurality of inlet holes arranged in the periphery of said irrigation cannula at angularly spaced locations about said longitudinal axis and within said reservoir portion.

19. An improved apparatus for supplying fluid to an aspirating fluid from a surgical site, said apparatus comprising:
   a handle support member having first and second closed opposite ends and a hollow intermediate interior region forming a resevoir;
   inlet means for supplying fluid to the hollow interior of said reservoir handle support member from said second end;
   outlet means in communication with said inlet means for conducting fluid out from said handle support member at said second end;
   first cannula means extending from an in fluid communication with said outlet means at said second end of said handle support member, through said hollow interior region and out through said first end, for aspirating fluid from a surgical site;
   second cannula means disposed circumscribedly about a portion of said first cannula means and terminating and extending from within said hollow interior region out through said first end of said support member, said second cannula means being radially spaced from said portion of said first cannula means to define a flow passage between said first and second cannula means, said second cannula means having a first opening to said flow passage positioned in fluid communication with said hollow interior portion of said support member, and a second opening to said flow passage positioned outside said support member beyond said first end;
   means securing said first and second cannula means together in fixed positional relation to one another;
   whereby said hollow support member interior intermediate region serves as a reservoir to hold and deliver fluid from said inlet means, and whereby pressurized fluid in said hollow support member interior portion is expelled therefrom through said first opening, said flow passage and said second opening.

20. The apparatus according to claim 19 wherein said second cannula means has tapered opposite end portions which contact and are secured to respective peripheral portions of said first cannula means.

* * * * *